United States Patent [19]
Kawesch

[11] Patent Number: 5,596,379
[45] Date of Patent: Jan. 21, 1997

[54] PORTABLE VISUAL ACUITY TESTING SYSTEM AND METHOD

[76] Inventor: Gary M. Kawesch, 4585 Stevens Creek Blvd., Santa Clara, Calif. 95051

[21] Appl. No.: 547,649

[22] Filed: Oct. 24, 1995

[51] Int. Cl.⁶ ................................. A61B 3/02; A61B 3/00
[52] U.S. Cl. ...................... 351/244; 351/239; 351/245; 351/246
[58] Field of Search ........................ 351/239, 244, 351/245, 246, 237, 222, 200; 250/201.2, 201.3, 201.4, 201.5, 201.6, 201.7, 201.8

[56] References Cited

U.S. PATENT DOCUMENTS

| | | | |
|---|---|---|---|
| H293 | 6/1987 | Task et al. | 351/243 |
| 4,408,846 | 10/1983 | Balliet | 351/203 |
| 4,764,006 | 8/1988 | Hamano et al. | 351/211 |
| 5,237,351 | 8/1993 | Kohayakawa | 351/243 |
| 5,398,085 | 3/1995 | Hofeldt | 351/243 |
| 5,420,652 | 5/1995 | Fujieda | 351/239 |
| 5,471,262 | 11/1995 | Trokel | 351/239 |

*Primary Examiner*—Hung Dang
*Attorney, Agent, or Firm*—Daniel J. Bourque; Kevin J. Carroll

[57] ABSTRACT

A portable visual acuity testing system and method is used to measure the visual acuity of a person being tested. The portable visual acuity testing system includes a portable visual acuity testing structure and a plurality of interchangeable image display cards adapted to be engaged with the structure. Each image display card includes one or more images, such as a Snellen letter or Allen figure, of a predetermined size. A distance measurer, such as an ultrasonic distance measuring device is included within the portable visual acuity testing structure. When the portable visual acuity testing device is positioned at a distance from the person being tested at which the person can see or visually recognize the image, the distance measurer is activated to automatically and accurately measure the distance to the person being tested. The portable visual acuity testing device includes built in circuitry for calculating a visual acuity level based on the measured distance and the predetermined size of the image, such as a "Snellen Equivalent," which can then be displayed on the portable visual acuity testing device.

20 Claims, 2 Drawing Sheets

PORTABLE VISUAL ACUITY TESTING SYSTEM AND METHOD

FIELD OF THE INVENTION

This invention relates to visual acuity measuring and testing systems and in particular, to a portable visual acuity testing system and method that automatically calculates a visual acuity level at various distances from the person being tested.

BACKGROUND OF THE INVENTION

Various techniques exist for measuring visual acuity which is typically represented by a "Snellen Equivalent," for example, 20/20, 20/25, 20/30, etc. (or 6/6, 6/8, 6/9 using the metric system). Measuring visual acuity is typically based on the size of a letter or symbol being viewed and the distance from the letter or symbol at which the person being tested can see or visually recognize the letter or symbol. According to the "Snellen Equivalent," the numerator or first number "20" (or "6") represents a 20 foot (or 6 meter) distance from the person being tested to the target, such as an eye chart. The denominator or second number refers to the size of the letter or symbol being viewed. For example, the 20/40 (or 6/12) letter on an eye chart is twice the size of the 20/20 (or 6/6) letter on the eye chart i.e. 18 mm vs. 9 mm. If the person being tested can see the 20 (or 6) size letter at 20 feet (or 6 meters) from the eye chart, that person is said to have 20/20 (or 6/6) vision.

The primary difficulty with using this standard for measuring visual acuity is the 20 foot distance limitation. Many eye examination rooms are not large enough to position the person being tested at 20 feet from the target or eye chart. Often, a mirror and projector system must be used to simulate a distance of 20 feet. Other expensive computerized systems can also be programmed for distances other than 20 feet. Even if such systems are used, the users often do not accurately measure the distances, resulting in inaccurate visual acuity measurements.

Another problem with traditional visual acuity measuring systems occurs when a person cannot see the largest letter or symbol on the chart. This is common when someone who wears glasses is being tested without their glasses. In these cases, the person being tested must often move toward the chart until they can read the letter or symbol and their distance from the chart must then be estimated. Other approaches to this problem have been to provide a small cube with a Snellen letter (e.g. E) and to move the letter toward the person being tested until the letter can be read. The distance from the letter to the person is then estimated, and the visual acuity is calculated, i.e. the "Snellen Equivalent."

The estimation of the distance between the person being tested and the eye chart or letter is typically crude and inaccurate. The resulting "Snellen Equivalent" calculated from the estimated distance is thus often an inaccurate measurement of visual acuity.

Accordingly, what is needed is a portable visual acuity testing system and method that allows visual acuity to be accurately and automatically tested without having to manually estimate distances or make calculations. The portable visual acuity testing system and method should avoid having to position the person being tested at a fixed distance from the testing device, and should avoid having to simulate the 20 foot distance with projectors or computers in an examination room that is too small. Moreover, the portable visual acuity testing system and method should provide the added flexibility of varying the sizes and types of the letters or symbols.

SUMMARY OF THE INVENTION

The present invention is directed to a visual acuity testing system and method that accurately and automatically tests the visual acuity of a person being tested at various distances. The visual acuity testing system includes a portable visual acuity testing device including a portable visual acuity testing structure and at least one image display portion having one or more images of a predetermined size. The portable visual acuity testing device also includes a visual acuity level measurer and reporter system for automatically measuring a visual acuity level of the person being tested.

The visual acuity level measurer and reporter system includes a distance measurer to measure a distance from the person being tested to the portable visual acuity testing structure when the person visually recognizes the image. A visual acuity level calculator is electrically coupled to the distance measurer to convert the predetermined size of the image and the measured distance into a visual acuity level. A visual acuity level display portion is electrically coupled to the visual acuity level calculator to display the visual acuity level.

In the preferred embodiment, the visual acuity testing system includes at least one removable image display portion or cards to be selected from a plurality of removable image display portions or cards having various sizes of images and various types of images, such as Snellen letters, Allen pictures, or a tumbling E. In this embodiment, the portable visual acuity testing structure is a portable visual acuity testing block having at least one image display card engaging region adapted to receive and engage an image display card having the image of a predetermined size. The portable visual acuity testing device includes a selected image display card removably engaged with the image display card engaging region on the portable visual acuity testing block.

According to the preferred embodiment, the visual acuity measurer and reporter includes an image size input receiver electrically coupled to the visual acuity level calculator, for inputting the predetermined size of the image on the selected image display card. Preferably, the image size input includes a series of electrical contacts disposed on the portable visual acuity testing block and adapted to contact corresponding electrical contacts arranged in a predetermined pattern on each image display card.

The distance measurer is preferably an ultrasonic distance measuring device including an emitter, for emitting an ultrasonic wave, a detector, for detecting the ultrasonic wave reflected off the person being tested, and a distance calculator responsive to the emitter and detector, for calculating the distance between the portable visual acuity testing structure and the person. An activation mechanism is electrically coupled to the distance measurer for activating the distance measurer when the image is visually recognized.

One embodiment also includes a sighting mechanism, for sighting the person being tested and assuring accurate measurements by the ultrasonic distance measuring mechanism, for example, a low-power laser that can be sighted on the person being tested.

The present invention also includes a method of testing visual acuity comprising the steps of: providing a portable acuity testing device; positioning the portable visual acuity testing device at a distance at which the person being tested is able to visually recognize the image; activating the distance measuring mechanism to measure the second distance at which the person being tested visually recognizes the image; converting the second distance and the predetermined size of the image into a visual acuity level, such as a "Snellen Equivalent;" and displaying the visual acuity level on the visual acuity level display portion. The preferred method includes first positioning the portable visual acuity testing device so that the person being tested is unable to visually recognize the image and then moving the portable visual acuity testing device to the distance at which the person visually recognizes the image.

The preferred method includes inserting a selected image display portion or card into the portable visual acuity testing device structure and inputting the predetermined size of the image into the visual acuity level calculator. The preferred method further includes interchanging a plurality of selected image display portions or cards each having an image of a different type or predetermined size depending on the needs and visual abilities of the person being tested.

DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
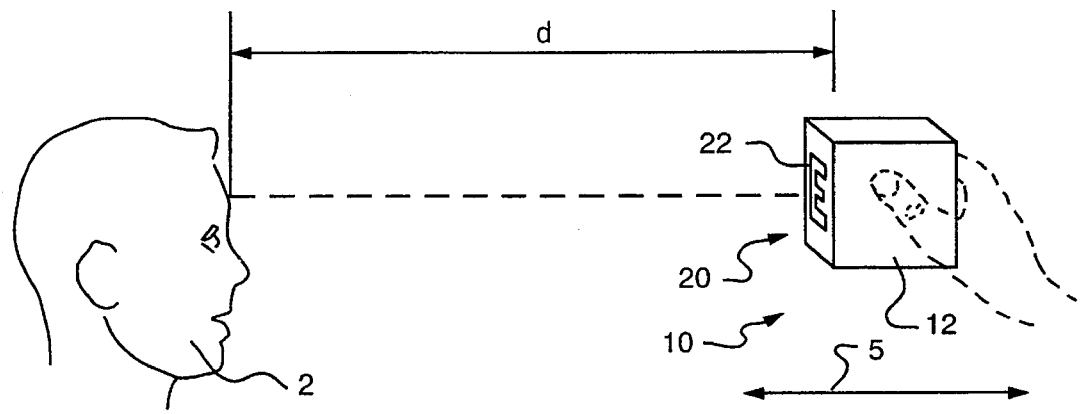
FIG. 1 is a side view of a portable visual acuity testing device according to the present invention as it is used to measure the visual acuity of a person being tested.

A portable visual acuity testing device 10, FIG. 1, according to the present invention, accurately tests the visual acuity of a person 2 and calculates their visual acuity level, for example, as represented by a "Snellen Equivalent"-20/20, 20/40, 20/100, etc. (or 6/6, 6/12, 6/30 using the metric system). The portable visual acuity testing device 10 includes a portable visual acuity testing structure 12, such as a block, and at least one image display portion 20 having an image 22, such as a Snellen letter, to be visually recognized by the person 2 being tested.

The portable visual acuity testing device 10, in one embodiment, can be used with a single image display portion 20 disposed on the portable visual acuity testing structure 12. The portable visual acuity testing device 10 can also be used as a visual acuity testing system with a plurality of interchangeable image display portions 20 each having various sizes and types of images 22. Each image display portion 20 in a visual acuity testing system is adapted to be removably engaged with the portable visual acuity testing structure or block 12, as will be described below.

The image 22 on the image display portion 20 is of a predetermined size, e.g. corresponding to a particular Snellen size Equivalent, so that if the image 22 can be visually recognized by the person 2 when the device 10 is positioned at a particular distance d from the person 2, that person will be determined to have a corresponding visual acuity. The portable visual acuity testing device 10 is capable of being moved within a testing area, in a direction 5 toward or away from the person 2, from a distance where the person 2 cannot visually recognize the image 22 to any distance from the person 2 until the person 2 visually recognizes the image 22. The preferred size of the image 22 is a size small enough so that the image 22 cannot be visually recognized by the person 2 at one distance within the testing area but large enough so that the image 22 can be visually recognized when moved to another distance d within the testing area. Visual acuity is most accurately measured when the visual acuity testing device 10 is positioned at the distance where the person 2 first visually recognizes the image 22.

The predetermined size of the image 22 and the distance d can then be automatically converted into a visual acuity level, such as a "Snellen Equivalent." For example, if the image 22 has a 20/100 Snellen size equivalent letter or symbol and cannot be read until positioned at a distance of 5 feet from the person 2 (e.g. 5/100), the "Snellen Equivalent" would be 20/400(5/100×4/4).

Figure 2:
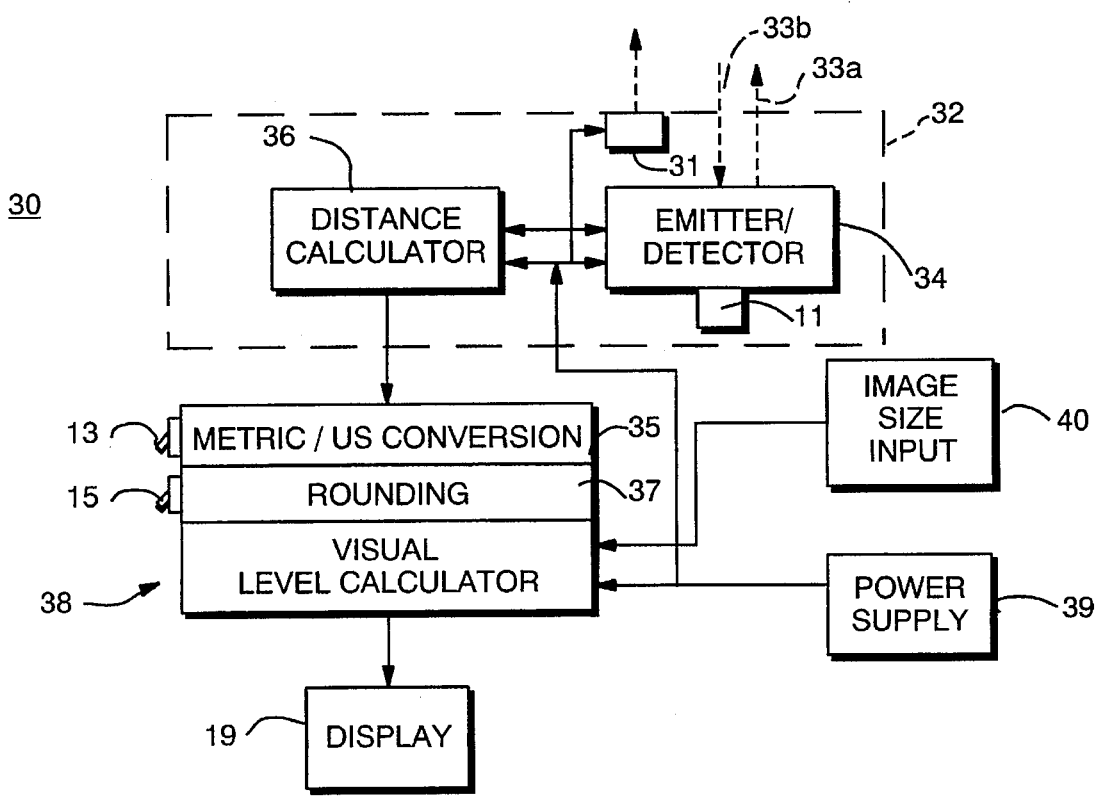
FIG. 2 is a block diagram of the portable visual acuity testing device according to the present invention.

The portable visual acuity testing device 10 according to the present invention further includes a visual acuity level measurer and reporter 30, FIG. 2, for automatically and accurately measuring the distance d from the person 2 to the portable visual acuity testing device 10 and calculating and displaying the visual acuity level, such as the "Snellen Equivalent." In the preferred embodiment, the visual acuity level measurer and reporter 30 includes circuitry built in to the portable visual acuity testing structure or block 12.

The visual acuity level measurer and reporter 30 includes a distance measurer 32 that measures the distance d from the person 2 being tested to the portable visual acuity testing device 10. The preferred embodiment includes a conventional ultrasonic distance measuring device having an ultrasonic emitter/detector 34. The ultrasonic emitter/detector 34 emits an ultrasonic wave 33a that is reflected off the person 2 being tested and detects the reflected ultrasonic wave 33b.

A distance calculator 36, responsive to the emitter/detector 34, calculates the distance traveled by the ultrasonic wave 33a, 33b. The distance measurer 32 preferably includes an activation mechanism 11, such as momentary contact button or switch, for activating the distance measurer 32 when the portable visual acuity testing device 10 is positioned at the distance d at which the person 2 being tested visually recognizes the image 22. An example of such an electronics distance measurer can be found in prior art carpenter ultrasonic "tape measures".

In one embodiment, the distance measurer 32 also includes a sighting mechanism 31, such as a low-power laser. The laser can be sighted on the person 2 being tested prior to or simultaneous with activating the distance measuring mechanism 32. When the laser sighting mechanism 31 is activated simultaneously with the distance measuring mechanism 32, the user can check to see if the laser is sighted on the person 2 and can ignore the distance reading if the laser is not sighted on the person 2. This assures that the distance d will be accurately measured from the person 2 and not from other interfering objects.

The visual acuity level measurer and reporter 30 further includes a visual acuity level calculator 38 electrically coupled to the distance measurer 32 and responsive to the image size input 40. The visual acuity level calculator 38 includes circuitry for calculating the visual acuity level, e.g. the "Snellen Equivalent" or other similar acuity level measurement, according to the measured distance d and the size of the image 22 on the image display portion 20. The circuitry for performing these calculations is within the knowledge of one skilled in the art.

The preferred embodiment of the visual acuity level calculator 38 includes a unit conversion portion 35, for calculating the visual acuity level in different units, such as a U.S. "Snellen Equivalent" of 20/20 or a metric "Snellen Equivalent" of 6/6. A unit selector 13 is coupled to the unit conversion portion 35 to allow the user to select a desired unit type, such as the U.S. measurement or the metric measurement. One example of the unit conversion portion 35 includes U.S./metric conversion circuitry known to those skilled in the art.

The preferred visual acuity level calculator 38 further includes a rounding portion 37 that "rounds" a calculated visual acuity level, for example, to the nearest tenth or one-hundredth unit. A rounding unit selector 15 is coupled to the rounding portion 37 so that a user can select the desired units for rounding the calculated visual acuity level. For example, a user can select the actual calculation, a calculated visual acuity level rounded to the tenth unit (e.g. 20/1246 to 20/1250) or rounded to the one-hundredth unit (e.g. 20/1246 to 20/1200). In one example, the rounding portion 37 includes circuitry for rounding calculations known to those skilled in the art.

The visual acuity level measurer and reporter 30 also includes a power supply 39. The preferred power supply 39 includes a long life battery, such as a watch battery.

One embodiment of the present invention features a visual acuity testing system having a plurality of interchangeable image display portions 20 with images 22 of different sizes. In such a system, an image size input receiver 40 is electrically coupled to the visual acuity level converter 38. The image size input receiver 40 receives the predetermined size of the image 22 on an image display portion 20 of the portable visual acuity testing device 10 when a selected image display portion 20 is engaged with the portable visual acuity testing structure or block 12, as will be discussed in greater detail below.

The portable visual acuity testing device further includes a visual acuity level display portion 19, electrically coupled to the visual acuity level calculator 38, for displaying the visual acuity level calculated by the visual acuity level calculator 38. For example, the visual acuity level display portion 19 can be an LCD, LED or other similar display.

Figure 3:
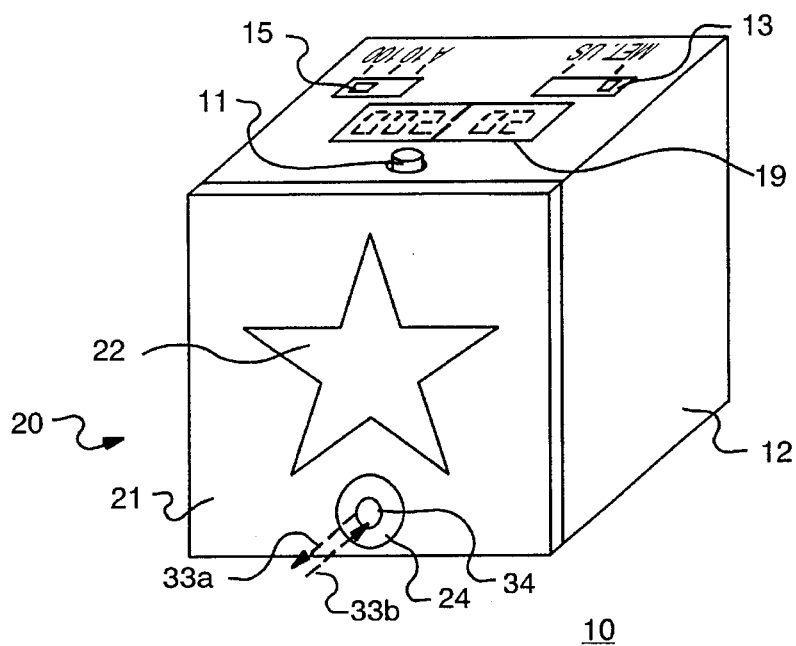
FIG. 3 is a perspective view of a portable visual acuity testing device according to one embodiment of the present invention.

In the preferred embodiment, the portable visual acuity testing block 12, FIG. 3, includes the activation mechanism 11, the unit selector 13, the unit rounding selector 15, and the visual acuity level display portion 19 located on a surface of the block 12. This allows a user to easily activate the portable visual acuity testing device 10, select and control the desired visual acuity level to be calculated, and to easily read the displayed visual acuity level. Preferably, the remaining portions of the distance measurer 32 and visual acuity level calculator 38 are located within the portable visual acuity testing block 12.

The preferred portable visual acuity testing device 10 further includes an aperture 24 extending through the portable visual acuity testing block 12 and the image display portion 20. The aperture 24 allows the emitted ultrasonic wave 33*a* and reflected ultrasonic wave 33*b* to be emitted and detected from the emitter/detector 34 located within the portable visual acuity testing block 12. If the portable visual acuity testing device 10 includes sighting mechanism, such as a low-power laser, the aperture 24 also allows the laser to be emitted from within the block 12.

Although the portable visual acuity testing block 12 shown is generally a cube shape, the present invention contemplates other shapes. The portable visual acuity testing block 12 is preferably of a size small enough to be hand held but large enough to accommodate image display portions 20 having larger letter sizes (e.g. 20/100, 20/200), for example approximately six inches by six inches.

The preferred embodiment of the image display portion 20 includes a removable image display card 21, FIG. 4, adapted to be temporarily held in place against one or more surfaces of the portable visual acuity testing block 12, as will be discussed in greater detail below. In this embodiment, a plurality of image display cards 21 having images 22 of various types and sizes can be used with the portable visual acuity testing device 10 as a visual acuity testing system. This visual acuity testing system can be used to test various persons having different needs and visual capabilities. For example, the larger size images can be used to measure the visual acuity of a person with poor vision and smaller size images can be used to measure the visual acuity of a person with good vision.

In addition to providing various sizes of images 22 on an image display card 21, the present invention contemplates different types of images. One type of image 22 includes Snellen letters corresponding to the various "Snellen Equivalent" sizes. For children or individuals who cannot read, instead of Snellen letters, symbols can be used on image display cards 21, such as a "tumbling E" or Allen pictures, e.g. a star, moon, car, tree, etc. (FIG. 3). The "tumbling E" and Allen pictures also have various sizes corresponding to the sizes of the standard Snellen letters. An image display card 21 can also include a single letter or symbol or a series of letters or symbols 22*a*, 22*b*, 22*c* of the same size. The present invention also contemplates letters or symbols in languages other than English.

In one embodiment, an image display card 21 includes images 22 on both sides of the image display card 21. An image display card 21 can include images 22 of different sizes on either side 26*a*, 26*b* of the image display card 21, or images of different types on either side 26*a*, 26*b* of the image display card 21, for example, a Snellen letter on one side 26*a*, and an Allen picture of the same size on the opposite side 26*b*. In this embodiment, the aperture 24*a* extending through the image display card is centrally located so that the aperture 24*a* aligns with an aperture through the portable visual acuity testing block 12 in both a first position where one side 26*a* of the image display card 21 is showing and a second position where the opposite side 26*b* of the image display card 21 is displayed.

Figures 4, 5:
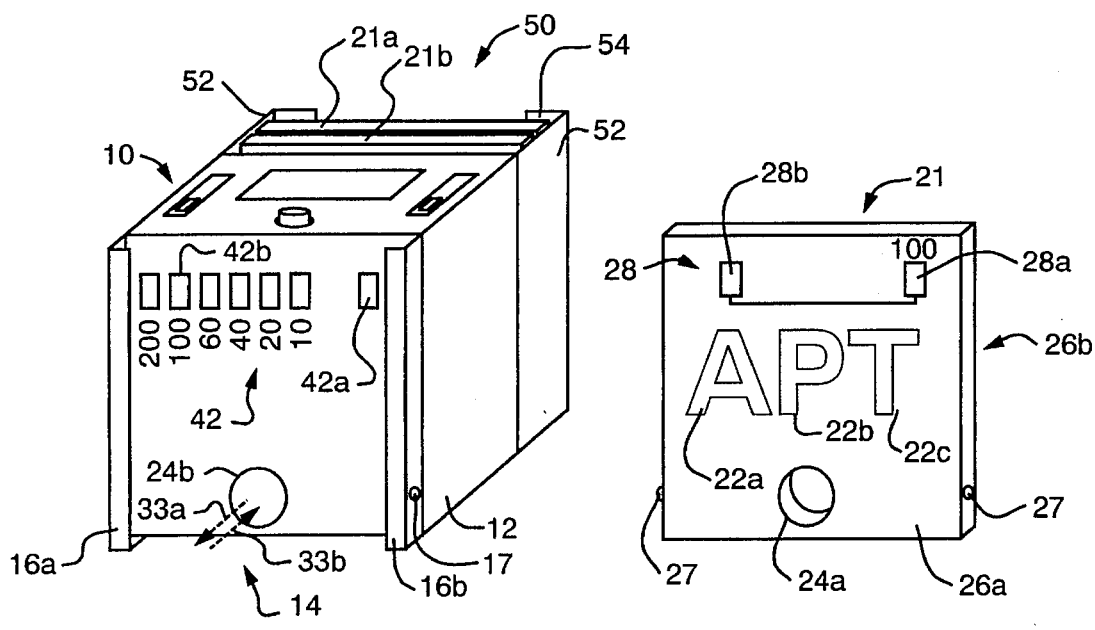
FIG. 4 is a perspective view of an image display card having a pattern of electrical contacts corresponding to the size of an image on the card and adapted to be engaged with the portable visual acuity testing block.
FIG. 5 is a perspective view of a portable visual acuity testing block having a series of electrical contacts for receiving an image size.

In the preferred embodiment, the portable visual acuity testing block 12, FIG. 5, includes an image display card engaging region 14 that receives and engages with a selected image display card 21. In one example, the engaging region 14 includes engaging flanges 16*a*, 16*b* for slidably receiving a selected image display card 21 and removably securing the image display card 21. The engaging flanges 16*a*, 16*b* preferably include a locking or securing mechanism, such as a detent or hole 17 on each flange 16*a*, 16*b* that engage with corresponding protrusions 27 on an image display card 21 (FIG. 4).

The preferred embodiment of the portable visual acuity testing block 12 used in a visual acuity testing system having a plurality of image display cards 21a, 21b includes an image display card storage region 50. The image display card storage region 50 holds or stores a plurality of image display cards 21a, 21b that are not currently being used on the portable visual acuity testing device 10. In one example, the image display card storage region 50 includes side portions 52 extending from the portable visual acuity testing block 12 to form an image display card storage region compartment 54 having a size capable of receiving and holding at least one additional image display card 21a.

The image size input receiver 40 in the preferred embodiment includes a series of electrical contacts 42 disposed generally on the image display card engaging region 14. Certain ones of the series of electrical contacts 42 are adapted to contact certain corresponding electrical contacts 28 on the selected image display card 21 so as to complete a circuit. Completing the circuit between certain contacts (image size input 40) indicates to the visual acuity level calculator 38 (FIG. 2) the predetermined size of the image on the selected image display card 21 engaged with the engaging region 14 of the block 12.

Each image display card 21, FIG. 4, includes at least two electrical contacts 28a, 28b corresponding to two electrical contacts 42b, 42a of the series of electrical contacts 42 on the engaging region 14 of the portable visual acuity testing block 12. The two electrical contacts 28a, 28b contact the corresponding electrical contacts 42b, 42a on the portable visual acuity testing block 12 and complete a circuit between the corresponding electrical contacts 42a, 42b, thereby inputting the predetermined size into the visual acuity level calculator 38. The first electrical contact 28a is common to each image display card 21. The location of the second electrical contact 28b depends on the predetermined size of the image on the image display card 21.

The two electrical contacts 28a, 28b disposed on one side 26a of the image display card 21 correspond to an image disposed on an opposite side 26b of the image display card 21 so that the two electrical contacts 28a, 28b contact the corresponding electrical contacts 42b, 42a to input the size of the image while that image is being displayed. If images 22 are disposed on both sides 26a, 26b of the image display card, electrical contacts 28a, 28b corresponding to the images 22 on both sides 26a, 26b are disposed on respective opposite sides 26b, 26a.

For example, an image display card 21 having an image with a 20/100 size will have a second electrical contact 28b in a location on the image display card 21 adapted to contact the corresponding second electrical contact 42a on the portable visual acuity testing block 12 corresponding to a predetermined size of 20/100. When the circuit between the corresponding second electrical contact 42b and the corresponding first electrical contact 42a is complete, the visual acuity level calculator 38 will register a size of 20/100.

Accordingly, when an image display card 21 is engaged with the engaging region 14 of the portable visual acuity testing block 12 electrical contacts 28a, 28b contact corresponding electrical contacts 42b, 42a, protrusions 27 engage with corresponding detents or holes 17, and image display card aperture 24a aligns with testing block aperture 24b. In the embodiment having images 22 on both sides 26a, 26b of an image display card 21, the image display card 21 can be turned over and engaged with the engaging region 14 in one of two positions. In either position, the electrical contacts on one side of the display card 21 contact corresponding electrical contacts on the visual engaging region 14, the image display card aperture 24a aligns with the testing block aperture 24b, and the protrusions 27 engage with the detents or holes 17. Other methods of selecting and indicating image size such as switch settings or a fixed size are considered within the scope of the invention.

The preferred method of the present invention includes positioning the portable visual acuity testing device 10 at a first distance from the person 2 being tested at which the person 2 is unable to see or visually recognize the image 22. The portable visual acuity testing device is then moved to a position where the person can see or visually recognize the image 22. At this point where the person visually recognizes the image, the user can activate the distance measurer 32, e.g. by depressing a button, and the distance measurer 32 measures the distance d from the person being tested. The visual acuity level calculator 38 calculates a visual acuity level, such as a Snellen Equivalent, and the visual acuity level is displayed on the visual acuity level display portion 19.

The preferred method further includes interchanging selected image display cards 21 and electrically connecting electrical contacts 28b, 28b on the image display card 21 with electrical contacts 42a, 42b on the portable visual acuity testing block 12. Image display cards 21 having various types and sizes of images can be interchanged according to the type of person being tested and that person's needs and visual abilities.

For example, image display cards 21 having different image sizes may be selected depending on the visual ability of the person being tested and the size of the testing area or room. If the person being tested has extremely poor vision, an image display card 21 having a large image size, e.g. 20/200, so that there is a location where the person actually visually recognizes the image. If the person's visual abilities are normal, but the testing area or room is limited in size, e.g. less than 20 feet in length, an image display card having a smaller image size, e.g. 20/10, may be selected so that the portable visual acuity testing device 10 can be moved, within the testing area, from the first distance where the image is not recognized to the second distance where the image is recognized.

Alternatively, the portable visual acuity testing device can be used to test one's own vision. The method of self-testing one's vision with the portable visual acuity testing device according to the present invention includes holding the portable visual acuity testing device and viewing the image in a mirror. The user moves to a location with respect to the mirror at which the user can visually recognize the image in the mirror. The user can then activate the distance measurer to measure the distance from the mirror.

Since the distance from the user to the mirror measured by the distance measurer is one-half the distance from the user to the image reflected in the mirror, the visual acuity level calculation must compensate for the difference. In one example, a self-testing image display card includes electrical contacts that indicate an image size that is half the image size of the image displayed. For example, an image display card having an image size of 20/40 includes electrical contacts that input a predetermined image size of 20/20 to the visual acuity level calculator. Inputting an image size that is one-half the actual size of the image displayed on the image display card accounts for the apparent image viewed in the mirror that is half the actual size of the image on the image display card. The present invention also contemplates having the distance calculator 36 or visual acuity level calculator 38 double the measured distance and a switch (not shown) that allows a user to select a self-test mode in which the distance is doubled.

Using the visual acuity testing device to self-test one's vision according to this method may also require a modified image on the self-testing image display card. For example, if Snellen letters are used on a self-testing image display card, the letters are reversed so that the mirror image of the letter is the correct orientation.

Accordingly, the portable visual acuity testing device provides a portable system and method for testing visual acuity regardless of the size of the examination room or the visual acuity level of the person being tested. The image size can be varied to test the visual acuity in any distance range rather than at a fixed distance of 20 feet. The portable visual acuity testing device further provides for an automatic and accurate measurement of the distance to avoid inaccurate estimated distances and inaccurate visual acuity level calculations.

Modifications and substitutions by one of ordinary skill in the art are considered to be within the scope of the present invention which is not to be limited except by the claims which follow.

What is claimed is:

1. A portable visual acuity testing device, for testing visual acuity of a person being tested at various distances from said person being tested, said portable visual acuity testing device comprising:
    a portable visual acuity testing structure including at least one image display portion having an image of a predetermined size; and
    a visual acuity level measurer and reporter disposed within said portable visual acuity testing structure, for automatically measuring and reporting a visual acuity level of the person being tested, said visual acuity level measurer and reporter including:
        a distance measurer, for measuring a distance from the person being tested to said portable visual acuity testing structure;
        a visual acuity level calculator, electrically coupled to said distance measurer and responsive to said predetermined size of said image, for calculating a visual acuity level based on said predetermined size of said image and said distance; and
        a visual acuity level display portion, electrically coupled to said visual acuity level calculator, for displaying said visual acuity level.

2. The portable visual acuity testing device of claim 1, further including an activation mechanism electrically coupled to said distance measurer, for selectively activating said distance measurer.

3. The portable visual acuity testing device of claim 1, wherein said at least one image display portion is removably coupled to said portable visual acuity testing structure, for allowing said at least one image display portion to be selected from among a plurality of interchangeable image display portions, wherein each interchangeable image display portion includes an image of a different size and an indicator representing a size of said image.

4. The portable visual acuity testing device of claim 3, further including an image size input receiver electrically coupled to said visual acuity level calculator, for inputting said indicator of each of said plurality of interchangeable image display portions as each interchangeable image display portion is engaged with said portable visual acuity testing structure.

5. The portable visual acuity testing device of claim 4, wherein said image size input receiver includes a series of electrical contacts disposed on said portable visual acuity testing structure and electrically coupled to said visual acuity level calculator, wherein said indicator representing said size of said image includes a predetermined pattern of electrical contact disposed on said at least one image display portion, and wherein selected contacts of said series of electrical contacts are adapted to contact certain of said electrical contacts arranged in said predetermined pattern on each of said plurality of interchangeable image display portions, wherein said predetermined pattern of said electrical contacts corresponds to said predetermined size of said image.

6. The portable visual acuity testing device of claim 1, wherein said distance measurer is an ultrasonic distance measuring device including an emitter, for emitting an ultrasonic wave, a detector, for detecting said ultrasonic wave reflected off the person being tested, and a distance calculator, responsive to said emitter and said detector, for calculating said distance between said portable visual acuity testing structure and the person being tested.

7. The portable visual acuity testing device of claim 6, further including a sighting mechanism, for sighting the person being tested and assuring accurate measurements from the person being tested by said ultrasonic distance measuring device.

8. The portable visual acuity testing device of claim 7, wherein said sighting mechanism includes a low-power laser.

9. The portable visual acuity testing device of claim 1, wherein said image on said at least one image display portion includes one of a Snellen letter, an Allen picture, and a tumbling E.

10. The portable visual acuity testing device of claim 1, wherein said visual acuity level calculator calculates a Snellen Equivalent.

11. The portable visual acuity testing device of claim 1, wherein said visual acuity level display portion includes an LED display.

12. A visual acuity testing system, for measuring visual acuity of a person being tested, said visual acuity testing system comprising:
    at least one removable image display card, each said at least one removable image display card having an image of a predetermined size;
    a portable visual acuity testing structure including an image display card engaging region, for receiving and engaging with said at least one removable image display card;
        an image size input receiver, for inputting said predetermined size of said image on said at least one removable image display card;
    a distance measurer, for measuring a distance from the person being tested to said portable visual acuity testing structure;
    a visual acuity level calculator, electrically coupled to said image size input receiver and said distance measurer, for calculating a visual acuity level based on said predetermined size of said image on said at least one removable image display card and said distance from the person being tested to said portable visual acuity testing structure; and
    a visual acuity level display portion, electrically coupled to said visual acuity level calculator, for displaying said visual acuity level.

13. A portable visual acuity testing block, comprising:

at least one image display card engaging region, adapted to receive and engage with an image display card;

an image size input receiver region, for receiving from an engaged image display card, an indication of a predetermined size of an image displayed on said engaged image display card;

a distance measurer, for measuring a distance from the person being tested to said portable visual acuity testing block, said distance measurer including an activation mechanism, for activating said distance measurer;

a visual acuity level calculator, electrically coupled to said image size input and said distance measurer activation mechanism, for calculating a visual acuity level based on said indication of said predetermined size of said image and said distance from the person being tested; and a visual acuity level display portion electrically coupled to said visual acuity level calculator, for displaying said visual acuity level.

14. A method of testing visual acuity comprising the steps of:

providing a portable visual acuity testing device including a portable visual acuity testing structure, an image display portion having an image of predetermined size, a distance measurer, a visual acuity level calculator coupled to said distance measurer, and a visual acuity level display portion coupled to said visual acuity level calculator;

positioning said portable visual acuity testing device at a distance at which the person being tested is able to visually recognize said image on said image display portion;

activating said distance measurer to measure said distance at which the person being tested visually recognizes said image on said image display portion;

calculating a visual acuity level based on said distance and said predetermined size of said image; and displaying said visual acuity level on said visual acuity level display portion.

15. The method of claim 14, further including first positioning said portable visual acuity testing device so that the person being tested is unable to visually recognize said image on said image display portion, and then moving said portable visual acuity testing device to said distance at which the person being tested visual recognizes said image on said image display portion.

16. The method of claim 14, wherein said step of providing a portable visual acuity testing device further includes the step of inserting a selected image display portion into said portable visual acuity testing structure, and inputting a predetermined size of said image on said selected image display portion into said visual acuity level calculator.

17. The method of claim 14, further including the step of sighting said distance measurer prior to activating said distance measurer, for assuring that said distance measurer measures said distance from the person being tested to said portable visual acuity testing device.

18. The method of claim 14, wherein said step of providing a portable visual acuity testing device further includes inserting a selected image display portion into said portable visual acuity testing structure and electrically connecting electrical contacts arranged in a predetermined pattern on said selected image display portion with selected electrical contacts of a series of electrical contacts on said portable visual acuity testing structure, whereby electrically connecting said electrical contacts arranged in a predetermined pattern completes a circuit inputting said predetermined size of said image to said visual acuity level calculator.

19. The method of claim 18, further including the step of interchanging a plurality of selected image display portions, each selected image display portion having an image of a different predetermined size and electrical contacts arranged in a different predetermined pattern.

20. The method of claim 14, wherein said step of calculating a visual acuity level includes calculating a Snellen Equivalent.

* * * * *